United States Patent [19]

Michel

[11] Patent Number: 4,550,721

[45] Date of Patent: Nov. 5, 1985

[54] FOOT SUPPORT

[76] Inventor: Lorraine M. Michel, 613 S. Walter Reed Dr., Apartment 611C, Arlington, Va. 22204

[21] Appl. No.: 510,318

[22] Filed: Jul. 1, 1983

[51] Int. Cl.⁴ .............................................. A61F 3/00
[52] U.S. Cl. .................................................. 128/80 E
[58] Field of Search ................... 128/80 E, 80 R, 581, 128/87 R, 89 R

[56] References Cited

U.S. PATENT DOCUMENTS

| | | | |
|---|---|---|---|
| 3,606,884 | 9/1971 | Peter | 128/80 E |
| 3,804,085 | 4/1974 | Eshuis et al. | 128/80 E |
| 3,916,886 | 11/1975 | Rogers | 128/80 E |
| 3,986,501 | 10/1976 | Schad | 128/80 E |

FOREIGN PATENT DOCUMENTS

| | | | |
|---|---|---|---|
| 479873 | 5/1916 | France | 128/80 E |
| 1442594 | 7/1976 | United Kingdom | 128/80 E |

*Primary Examiner*—John D. Yasko
*Attorney, Agent, or Firm*—Lane and Aitken

[57] ABSTRACT

A support for maintaining a wearer's foot at approximately a right angle with the leg includes a shoe having a brace fixedly connected or integrally formed therewith. The shoe has a sole and an upper which includes a posterior aspect and which covers a portion of the leg of the wearer. The brace has a vertical part that is disposed adjacent to the posterior aspect of the shoe and a horizontal part that is adjacent to the sole of the shoe. The brace is substantially rigid and the surface of the brace that is, when used, adjacent to the wearer's foot is provided with a means for releasably engaging the foot or an article of wearing apparel covering the foot. An elastic support, connected to a portion of the upper which is adjacent to the metatarsus or phalanges of the foot and also connected to the upper adjacent to the wearer's leg, is also provided.

16 Claims, 10 Drawing Figures

FOOT SUPPORT

BACKGROUND OF THE INVENTION

This invention relates to a support for maintaining a wearer's foot at approximately a right angle with the wearer's leg.

Many people suffer from an inability to independently maintain a foot in a neutral position, i.e., at approximately a right angle with the leg. This malady can be caused by damage to the peroneal nerve, which normally controls the muscles which allow the neutral position to be maintained. The peroneal nerve can fail to function properly due to congenital defects, illnesses such as polio, or accidents which result in a stretching or tearing of the nerve. The malady can also result from muscular dysfunction or atrophy, such as that occasioned by extended confinement to a horizontal, bedridden position. Regardless of the cause, these individuals are unable to maintain their foot in a neutral position against the force of gravity, and are said to suffer from "foot drop" or "toe drop".

Numerous attempts have been made in the past to satisfactorily provide support for patients suffering from this malady. Braces have been employed which extend from the foot to an area just below the knee, but such devices suffer from the fact that they greatly restrict the user's movement, are cumbersome, heavy, conspicuous and uncomfortable. Other devices have resembled a posterior splint made from plastic and having a high calf-engaging upper portion, a narrow heel-engaging portion and an integral foot-engaging lower portion, wherein the splint approximates a right angle. The splint is not connected to a shoe, but the user instead typically wears the splint inside or outside of a sock and places the splint in a shoe. This arrangement suffers from a sliding action not only between the support and the wearer's foot, but also between the shoe and the support. This deficiency can become a very significant problem when the shoe is worn when the wearer undergoes vigorous activity, such as when playing basketball, jogging, or walking briskly. Other alternatives for athletes suffering from foot drop have included the taping of the leg and foot adjacent to the ankle to thus lock the ankle into a desired position. A problem with this technique has included discomfort, interruption of circulation, and inability to effectively retain the foot in a neutral position.

Thus, it can be seen that there is a need in the art for a support for maintaining a wearer's foot at approximately a right angle with the leg, such that the support is comfortable to wear, unrestrictive of the wearer's movements, compact in size, and conducive to sureness of footing.

SUMMARY OF THE INVENTION

It has now been found that the deficiencies of the prior art can be overcome by providing a support for maintaining a wearer's foot at approximately a right angle with the leg which includes a shoe having a brace fixedly connected or integrally formed therewith. The shoe has a sole and an upper which includes a posterior aspect and which covers a portion of the leg of the wearer. The brace has a vertical part that is disposed adjacent to the posterior aspect of the shoe and a horizontal part that is adjacent to the sole of the shoe. The brace is substantially rigid and the surface of the brace that is, when used, adjacent to the wearer's foot is provided with a means for releasably engaging the foot or an article of wearing apparel covering the foot. An elastic support, fixedly connected to a portion of the upper which is adjacent to the metatarsus or phalanges of the foot and releasably connected to the upper adjacent to the wearer's leg, is also provided.

DESCRIPTION OF THE PREFERRED EMBODIMENTS

Figure 1:
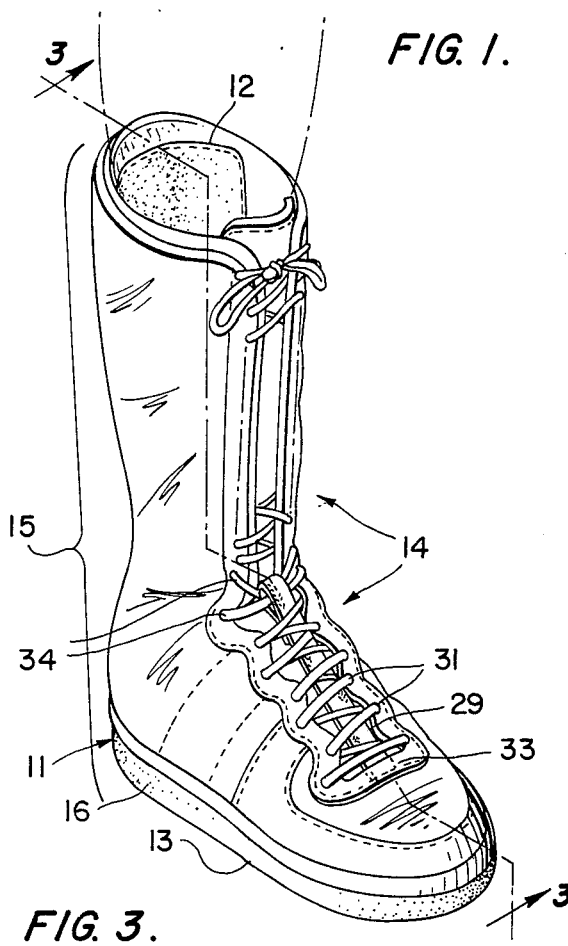
FIG. 1 is a perspective view of a support in accordance with the invention, with the wearer's leg depicted in phantom and some lacing cut away.

Referring now more specifically to the invention, as depicted in the attached drawings, the support consists of a shoe 11 and a brace 12. The shoe includes a sole 13 and an upper, generally referred to by reference numeral 14. The upper is that part of the shoe extending upward from the sole, and it includes a posterior aspect 15 that extends from heel 16 of the sole to top 17 of the shoe. As can be seen in the drawings, upper 14 is high enough to encircle a portion of the wearer's leg which is adjacent to the ankle. The portion of the leg that is encircled should be large enough so that the portion of the brace that is adjacent to the leg will be adequately and comfortably supported. For use in vigorous athletic activity, such as basketball, a height from the heel to the top of the shoe of 10 or 11 inches may be satisfactory for an athlete who is about 6' 11". In general, the height of the shoe should reach the bottom of the calf muscle.

Figure 3:
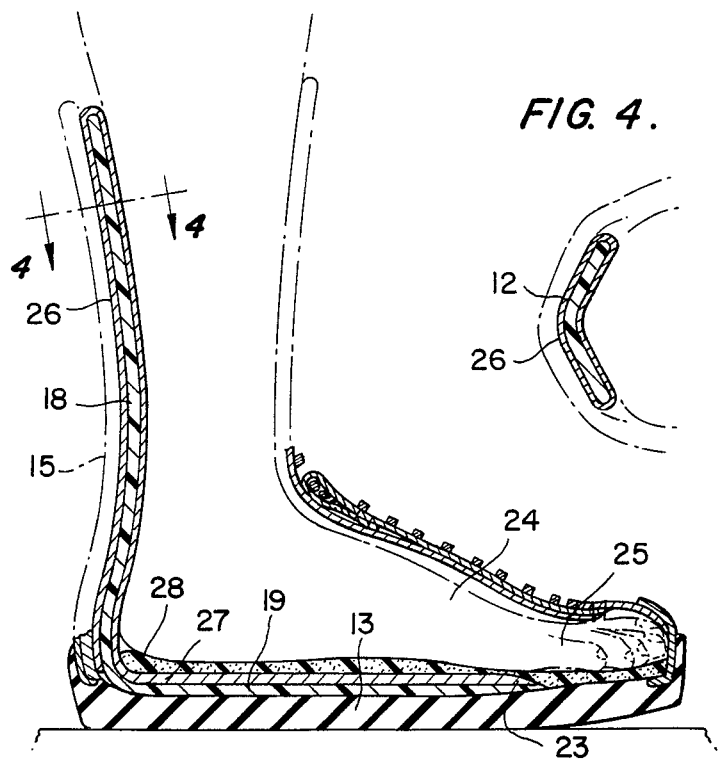
FIG. 3 is a sectional view taken along plane 3—3 of FIG. 1.
Figure 4:
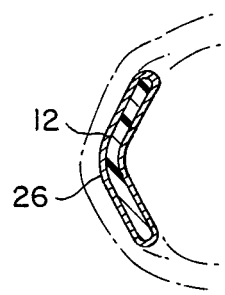
FIG. 4 is a sectional view taken along line 4—4 of FIG. 3.
Figure 5:
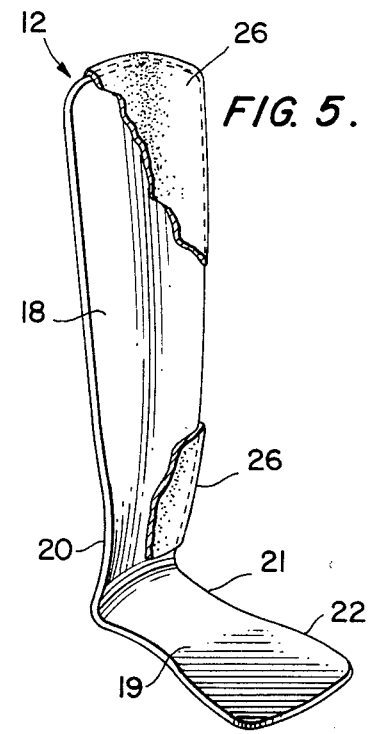
FIG. 5 is a perspective view of a brace, with a covering of the brace depicted in cut away fashion.

As best depicted in FIGS. 3 and 5, brace 12 includes a vertical part 18 and a horizontal part 19. The vertical part is disposed adjacent to the posterior aspect 15 of the shoe and the horizontal part is disposed adjacent to the sole 13. The brace can be generally contoured to fit the wearer's foot. Thus, as depicted in FIG. 5, the brace is shaped inwardly near an ankle portion 20, narrowed at a heel portion 21, and broadened at a sole portion 22. Preferably, the horizontal and vertical parts of the brace will not meet at a right angle, but the intersection will instead be curved. As depicted in FIG. 4, the brace can also be curved to shape the curve of the wearer's leg. It is also possible to form fit the brace and shoe to fit a specific wearer's foot and leg, in accordance with methods known in the art. As depicted in FIG. 3, it can be seen that the end 23 of the brace occurs between the metatarsus 24 and phalanges 25 of the foot.

Figure 2:
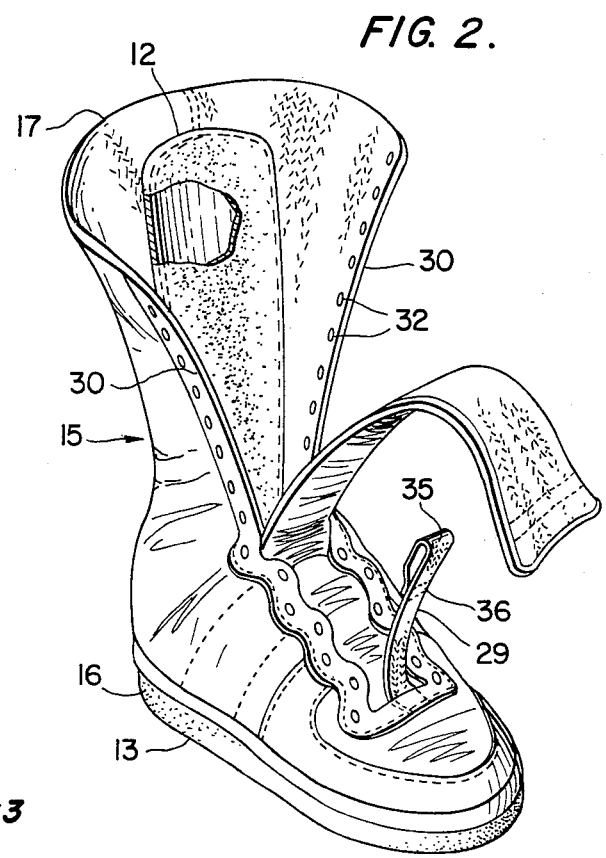
FIG. 2 is a perspective view of the support depicted in FIG. 1 before it is applied to the wearer's foot.

The brace is fixedly connected to the shoe, or is built into the shoe. Preferably, the fixed connection occurs along the interface between the horizontal part 19 of the brace and the sole 13. A fixed connection can also be made between the posterior aspect 15 and vertical part of the brace in an area adjacent to the wearer's ankle. Preferably, the brace will not be fixedly connected to the shoe adjacent to the top 17 of the shoe so that, as depicted in FIG. 2, the top of the shoe can be separated from the brace when it is not laced up. This provision facilitates the application and removal of the shoe. The fixed connection can be effected by any suitable means known in the art, such as by bonding, gluing or tacking. It is also conceivable that the brace and sole of the shoe could be initially formed in an integral relationship. If added cushioning is desired, it can be provided by, inter alia, the addition of air pockets between the horizontal part 19 and sole 13.

The shoe can be composed of any suitable materials commonly used in the art. The selection of suitable materials will depend in part upon the nature of use to which the shoe will be put. Thus, if the shoe is an athletic shoe, it would be generally desirable for the sole to afford sufficient traction between the wearer's foot and a playing surface, and the upper should preferably be provided with means for ventilation. In the case of a street shoe, the sole would preferably be denser and more rigid. In either case, the upper could be composed of leather or canvas, as well as a wide variety of other natural and synthetic flexible materials known to the art. The brace can be formed of any substantially rigid material that will provide support for the foot. The rigidity of the brace can vary depending upon the weight of the foot that it will support. Also, the rigidity can vary, depending upon the provision for auxilliary supports, such as the elastic support discussed hereinbelow. Preferably, the support will be composed of a substantially rigid plastic, such as polypropylene.

In order to prevent sliding between the brace and the wearer's foot or a piece of wearing apparel, such as a sock or nylon, covering the wearer's foot, means are provided for releasably engaging the brace and the foot or the wearing apparel. The releasable engagement can be effected by a number of means, including that depicted in FIGS. 3 to 5. In these figures, it can be seen that a covering 26 has been applied to the vertical part 18 of the brace. The covering extends from the heel area to the top of the brace, and can be composed of any material, such as a chamois-like fabric, that will allow some frictional engagement between the brace and the wearer's foot and calf, or between the brace and an article of wearing apparel.

The means for releasably engaging the wearer's foot or sock or the like can also be positioned adjacent to the horizontal part 19 of the brace. As depicted in FIG. 3, this can involve a provision for a substantially rigid and substantially non-deformable insert 27 and a deformable insert 28. The non-deformable insert 27 should not slide with relation to the brace or deformable insert 28, and this non-sliding relationship can be established by frictional, adhesive, or other means known in the art. Insert 27 can be composed of a large number of materials, such as cellulosic or plastic materials. The deformable insert 28 can be composed of any shock-absorbing and comfort-inducing material which is known in the art. Of course, many modifications in this arrangement will be apparent, such as the elimination of the non-deformable insert 27, whereby the deformable insert 28 would be held in a non-sliding relationship with horizontal part 19 of the brace.

As depicted in FIG. 3, the means for releasably engaging the foot or article of wearing apparel can include both the covering 26 and the insert 27, 28 arrangement. Other means for providing the releasable engagement can include the formation of a textured surface on brace 12 which acts to induce frictional engagement with the foot or sock or the like. Also, the brace can be imbedded in layers of the shoe wall, wherein the inner layer of the wall adjacent to the wearer's foot will itself provide the releasable engagement. Regardless of the means selected for providing the releasable engagement, it should prevent sliding between the wearer's foot and the support, to provide greater sureness of footing and to both render the individual more effective in his or her footwork and to reduce the possibility for injury. This beneficial result will be readily apparent in sports applications, such as basketball, track, football, soccer, and the like, but it can also be important in applications relating to street use.

The provision for brace 12 may, in some cases, provide all the support necessary for maintaining the foot in a neutral position. However, in a preferred embodiment, an additional support is provided at the front of the shoe to cause a tensioning between a portion of the shoe which is adjacent to the leg and a portion of the shoe which is adjacent to the foot.

One type of auxilliary elastic support is depicted in FIGS. 1 through 3. Here, an elastic support 29 is provided in a leather shoe in which the upper 14 is separated along the leg and metatarsus area to form sides 30 which are drawn together with laces 31 through eyelets 32. Elastic support 29 is securely fastened to a portion 33 of the upper by stitching. The elastic support is then positioned under the lacing adjacent to the metatarsus and is then looped around a number of laces 34 which are located just above the wearer's foot on the wearer's leg. Loop 35 can be formed by stitching 36, so that the shoe lace is laced through the loop as the shoe is being laced up. The elastic support can advantageously be secured during dorsiflexion.

It will be readily apparent that a significant amount of pressure will be exerted on elastic support 29. Accordingly, the elastic support should be very strong and it should be very securely attached. The elastic support should be soft so that it will not be uncomfortable for the wearer. Also, the elastic support should be sufficiently distendable to thus allow the wearer to plantarflex the foot, so that, for example, an athlete would be able to better push off with the toes. A suitable material for the elastic support can be a strong, elastic nylon material. While FIGS. 1 through 3 depict two means of attachment at either end of the elastic support, it will be readily apparent that many other means of attachment will be possible, and that the positions of the fixed connection and releasable connection can be reversed.

Figure 6:
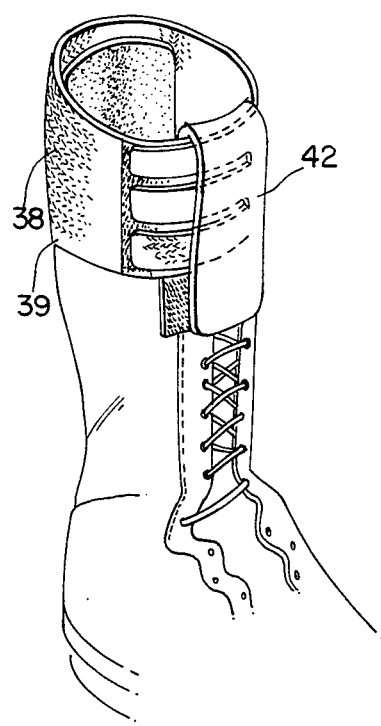
FIG. 6 is a perspective view of a portion of a support in accordance with a second embodiment with some lacing cut away.
Figure 7:
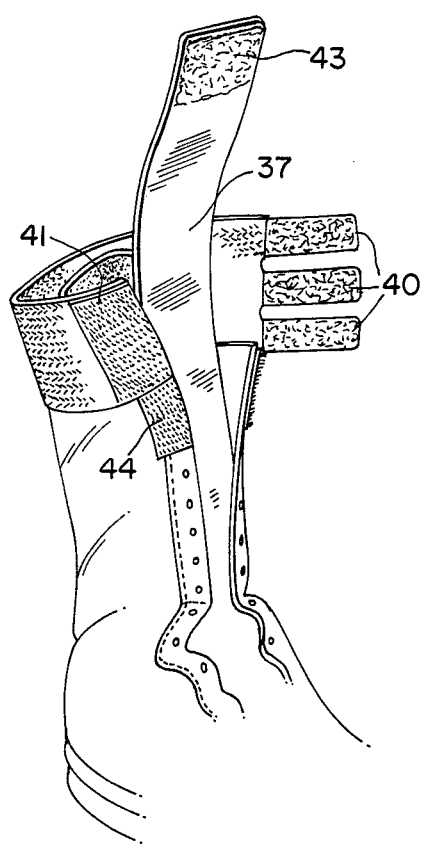
FIG. 7 is a perspective view of the support of FIG. 6, before being applied to a foot.

In FIGS. 6 and 7, another embodiment of the auxilliary support is demonstrated. In this embodiment, the tongue 37 is itself the elastic support. Thus, it is pulled up tightly by the wearer, preferably during dorsiflexion, and is then attached adjacent to the top of the shoe. The characteristics of tongue 37 should be the same as those for the elastic support 29 of the above embodiment, and means of attaching the tongue can be similarly varied.

In FIGS. 6 and 7, a preferred means for attaching tongue 37 to the top of the shoe is depicted. In this embodiment, the height of the shoe has been extended by the addition of extension 38, which has been attached by stitching 39. Extension 38 can provide more support for the brace arrangement than that which would normally be afforded by a regular high top tennis shoe. It is preferably a strong, flexible material such as canvas. The extension can also be made of leather and be simply a continuation of the upper of the shoe.

In the embodiment depicted in FIGS. 6 and 7, straps 40 are provided on extension 38. The straps can be sewn or otherwise attached to the extension 38, or they can be formed as an integral part of the extension. The straps should be composed of a strong, durable material, such as leather or canvas. In the drawings, the straps 40 are attached to one side of the upper and are provided with a Velcro surface on the inside which is arranged to coincide with the cooperating Velcro surface 41 that is disposed on the other side of the upper.

After straps 40 have been securely affixed around the base of the calf muscle to Velcro portion 41, tongue 37 is tensioned by pulling up on the tongue, and the tongue is then releasably attached to the upper by folding portion 42 over straps 40 and affixing Velcro portion 43 of the tongue to Velcro portion 44 of the upper. Of course, while Velcro has been disclosed as a suitable means for affixing the straps and the tongue, it will be readily apparent that many other types of fastening means, such as snaps, buttons and the like, can be used.

Figure 8:
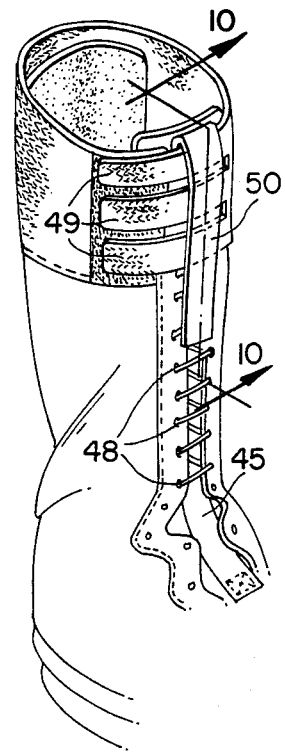
FIG. 8 is a perspective view of still another embodiment of a support with some lacing cut away.
Figure 9:
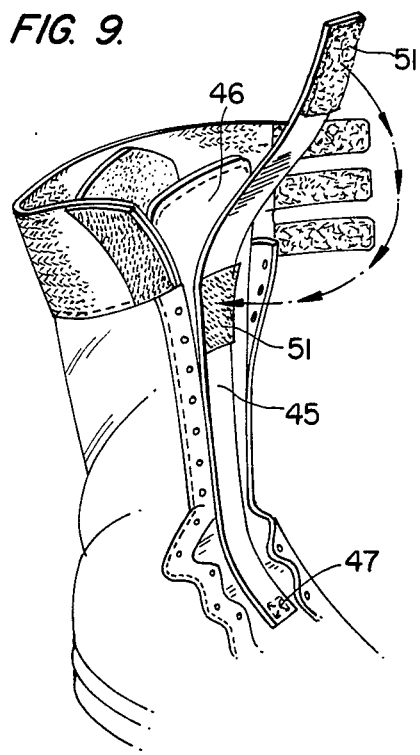
FIG. 9 is a perspective view of the support of FIG. 8 before being applied to a foot.
Figure 10:
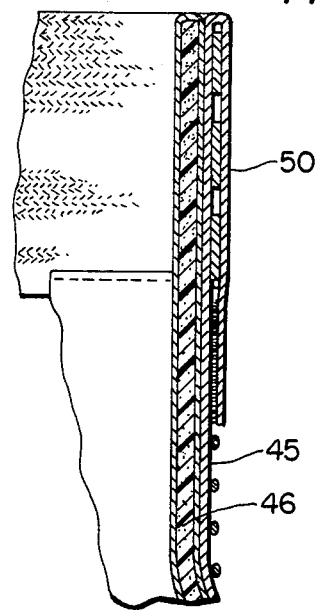
FIG. 10 is a sectional view taken along plane 10—10 of FIG. 8.

Still another embodiment for providing the auxilliary elastic support is depicted in FIGS. 8 through 10. Here, an elastic support 45 is fixedly attached to tongue 46 by stitching 47, and is then placed underneath lacing 48 and drawn up above straps 49. After straps 49 are securely fastened, elastic support 45 is tensioned and a portion 50 of the elastic support is drawn over the flaps, as indicated by the arrow in FIG. 9, and secured by means of Velcro portions 51.

In the preferred embodiment, as described, brace 12 cooperates with the elastic support to maintain the foot in a neutral position and to bring the foot back to a neutral position in the event that a plantarflex of the foot causes the angle between the leg and foot to be greater than 90°. Since these two supporting features cooperate, it will be readily apparent that greater support by one can be offset by lesser support by the other.

The support that has been described can be used in the field of athletics, such as in basketball shoes, football shoes, running and track shoes and the like. It can also be used in casual and dress street shoes. Suitable modifications to adapt the invention to each of these fields of use will be readily apparent to those of ordinary skill in the art.

Having thus described the invention with regard to a number of specific embodiments, it will be readily apparent to those of ordinary skill in the art that numerous modifications can be made without departing from the scope of the present invention.

I claim:

1. A support for maintaining a wearer's foot at approximately a right angle with the wearer's leg comprising (a) a shoe having a sole and an upper which comprises a posterior aspect and which covers a portion of the leg and (b) a brace having a vertical part disposed adjacent to said posterior aspect and a horizontal part adjacent to said sole, wherein
    said brace is substantially rigid and fixedly connected to said shoe,
    a surface of said brace which is adjacent the foot is provided with a means for releasably engaging the foot or an article of wearing apparel covering the foot,
    said upper further comprises an elastic support connected to a first portion of said upper which is adjacent to the metatarsus or phalanges of the foot, and connected to a second portion of said upper which is adjacent to the leg,
    a portion of said upper adjacent to the leg is divided substantially vertically to form two sides and said sides are releasably connected with lacing, and
    said elastic support is disposed underneath said lacing.

2. The support according to claim 1, wherein said brace and said shoe are integrally connected and said means for releasably engaging comprises a layer of said shoe.

3. The support according to claim 1, wherein said means for releasably engaging is a texture of said surface.

4. The support according to claim 1, wherein said means for releasably engaging comprises an insert disposed adjacent to said horizontal part.

5. The support according to claim 1, wherein the area of the foot supported by said brace consists of the heel and metatarsus of the foot.

6. The support according to claim 1, wherein said brace is plastic.

7. The support according to claim 1, wherein an inside surface of the support which is adjacent to the foot is molded to correspond to the shape of the foot.

8. A support for maintaining a wearer's foot at approximately a right angle with the wearer's leg comprising (a) a shoe having a sole and an upper which comprises a posterior aspect and which covers a portion of the leg and (b) a brace having a vertical part disposed adjacent to said posterior aspect and a horizontal part adjacent to said sole, wherein
    said brace is substantially rigid and fixedly connected to said shoe,
    a surface of said brace which is adjacent the foot is provided with a means for releasably engaging the foot or an article of wearing apparel covering the foot,
    said upper further comprises an elastic support connected to a first portion of said upper which is adjacent to the metatarsus or phalanges of the foot, and connected to a second portion of said upper which is adjacent to the leg,
    a portion of said upper adjacent to the leg is divided substantially vertically to form two sides,
    said upper further comprises at least one strap fixedly connected to one of said sides and releasably connected to the other of said sides, and
    said elastic support is elongated, such that an uppermost portion of said elastic support can be extended over the top of said strap and an end of said elastic support which is extended over can be releasably connected to said second portion.

9. The support according to claim 8, wherein said second portion is disposed on said elastic support.

10. A support for maintaining a wearer's foot at approximately a right angle with the wearer's leg comprising a shoe having a sole and an upper, said upper covering a portion of said leg and comprising an elastic support connected to a first portion of said upper that is adjacent to the metatarsus or phalanges of the foot and connected to a second portion of said upper that is adjacent to the leg, and, further, wherein a portion of said upper adjacent to the leg is divided substantially vertically to form two sides, said sides being releasably connected with lacing and said elastic support being disposed underneath said lacing.

11. The support according to claim 10, wherein said shoe is an athletic shoe.

12. The support according to claim 10, wherein said shoe is a street shoe.

13. The support according to claim 10, wherein said elastic support is a tongue of said shoe.

14. The support according to claim 10, wherein said second portion is disposed at the top of said upper.

15. A support for maintaining a wearer's foot at approximately a right angle with the wearer's leg comprising a shoe having a sole and an upper, said upper covering a portion of the leg and comprising an elastic support connected to a first portion of said upper that is adjacent to the metatarsus or phalanges of the foot and connected to a second portion of said upper that is adjacent to the leg, wherein a portion of said upper adjacent to the leg is divided substantially vertically to form two sides, wherein said upper further comprises at least one strap fixedly connected to one of said sides and releasably connected to the other of said sides, and wherein said elastic support is elongated, such that an uppermost portion of said elastic support can be extended over the top of said strap and an end of said elastic support that is extended over can be releasably connected to said second portion.

16. The support according to claim 15, wherein said second portion is disposed on said elastic support.

* * * * *